(12) United States Patent
Miyao et al.

(10) Patent No.: US 9,328,429 B2
(45) Date of Patent: May 3, 2016

(54) METHOD FOR EVALUATING DEGREE OF CRYSTAL ORIENTATION IN POLYCRYSTALLINE SILICON, SELECTION METHOD FOR POLYCRYSTALLINE SILICON RODS, AND PRODUCTION METHOD FOR SINGLE CRYSTAL SILICON

(71) Applicant: Shin-Etsu Chemical Co., Ltd., Tokyo (JP)

(72) Inventors: Shuichi Miyao, Niigata (JP); Junichi Okada, Niigata (JP); Shigeyoshi Netsu, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/389,912

(22) PCT Filed: Mar. 29, 2013

(86) PCT No.: PCT/JP2013/002178
§ 371 (c)(1),
(2) Date: Oct. 1, 2014

(87) PCT Pub. No.: WO2013/150758
PCT Pub. Date: Oct. 10, 2013

(65) Prior Publication Data
US 2015/0047554 A1  Feb. 19, 2015

(30) Foreign Application Priority Data
Apr. 4, 2012 (JP) ................................. 2012-085528

(51) Int. Cl.
*C30B 33/00* (2006.01)
*C30B 13/34* (2006.01)
(Continued)

(52) U.S. Cl.
CPC .................. *C30B 13/34* (2013.01); *C01B 33/02* (2013.01); *C23C 16/24* (2013.01); *C30B 25/02* (2013.01);
(Continued)

(58) Field of Classification Search
CPC ................................. C30B 33/00; C30B 29/04
See application file for complete search history.

(56) References Cited

U.S. PATENT DOCUMENTS

| 5,136,624 A | 8/1992 | Schneider et al. |
| 6,678,347 B1 | 1/2004 | Kozaczek et al. |

(Continued)

FOREIGN PATENT DOCUMENTS

| CN | 1487285 A | 4/2004 |
| CN | 102498064 A | 6/2012 |

(Continued)

OTHER PUBLICATIONS

International Search Report Issued Jun. 4, 2013 in PCT/JP13/002178 Filed Mar. 29, 2013.

(Continued)

*Primary Examiner* — Robert M Kunemund
(74) *Attorney, Agent, or Firm* — Oblon, McClelland, Maier & Neustadt, L.L.P.

(57) ABSTRACT

When a plate-like sample 20 extracted from a polycrystalline rod is evaluated, peaks can appear in a φ-scanning chart. The smaller the number of such peaks, and the narrower the half-value width of the peak, the more suitable the polycrystalline silicon rod is as a raw material for producing single-crystal silicon. It is preferable that the number of peaks in the φ-scanning chart is, for both the Miller index planes <111> and <220>, equal to or smaller than 24/cm² when converted into unit per area of the plate-like sample. It is also preferable that the value obtained by multiplying the peak half-value width by $\delta L = 2^{1/2} \pi R_0 / 360$, where $R_0$ is the radius of the sample, is defined as an inhomogeneous crystal grain size, and that a polycrystalline silicon rod of which all the inhomogeneous crystal grain sizes are smaller than 0.5 mm is selected as a raw material for producing single-crystal silicon.

19 Claims, 6 Drawing Sheets

(51) Int. Cl.

| | |
|---|---|
| *C30B 29/06* | (2006.01) |
| *G01N 23/207* | (2006.01) |
| *C30B 35/00* | (2006.01) |
| *C01B 33/02* | (2006.01) |
| *C23C 16/24* | (2006.01) |
| *C30B 25/02* | (2006.01) |
| *C30B 13/00* | (2006.01) |
| *C30B 15/00* | (2006.01) |

(52) U.S. Cl.
CPC .............. *C30B 29/06* (2013.01); *C30B 35/007* (2013.01); *G01N 23/207* (2013.01); *C01P 2002/60* (2013.01); *C01P 2002/74* (2013.01); *C30B 13/00* (2013.01); *C30B 15/00* (2013.01)

(56) References Cited

U.S. PATENT DOCUMENTS

| 8,049,100 B2 * | 11/2011 | Clark et al. ............... 136/257 |
|---|---|---|
| 2004/1017700 | 9/2004 | Yokoyama et al. |
| 2008/0286550 A1 | 11/2008 | Sofin et al. |
| 2012/0175613 A1 | 7/2012 | Netsu et al. |
| 2013/0102092 A1 | 4/2013 | Netsu et al. |
| 2014/0033966 A1 | 2/2014 | Miyao et al. |

FOREIGN PATENT DOCUMENTS

| JP | 37 18861 | 12/1962 |
|---|---|---|
| JP | 4 22218 | 4/1992 |
| JP | 2005 534028 | 11/2005 |
| JP | 2005-534028 A | 11/2005 |
| JP | 2006 71377 | 3/2006 |
| JP | 2007 240192 | 9/2007 |
| JP | 2008-532315 A | 8/2008 |
| JP | 2008 249605 | 10/2008 |
| JP | 2008 285403 | 11/2008 |
| JP | 2010-540395 A | 12/2010 |
| JP | 2012-17997 A | 1/2012 |
| WO | 2004 011919 | 2/2004 |
| WO | 2012 164803 | 12/2012 |

OTHER PUBLICATIONS

Office Action issued May 12, 2015 in Japanese Patent Application No. 2012-085528.
European Search Report dated Feb. 16, 2016 issued in corresponding European patent application No. 13772580.0.

\* cited by examiner

METHOD FOR EVALUATING DEGREE OF CRYSTAL ORIENTATION IN POLYCRYSTALLINE SILICON, SELECTION METHOD FOR POLYCRYSTALLINE SILICON RODS, AND PRODUCTION METHOD FOR SINGLE CRYSTAL SILICON

TECHNICAL FIELD

The present invention relates to a method for evaluating a degree of crystal orientation of polycrystalline silicon, and a selection method, using this evaluation method, of a polycrystalline silicon rod which is used as a raw material for producing single-crystal silicon. More particularly, the present invention relates to a technology for selecting a non-oriented polycrystalline silicon rod which is suitable for stable production of single-crystal silicon.

BACKGROUND ART

Crystals of monocrystalline silicon which is essential for production of semiconductor devices, etc. are grown by a method such as the CZ method or the FZ method, and a polycrystalline silicon rod or a polycrystalline silicon ingot is used as the raw material. Such a polycrystalline silicon material is in most cases produced by the Siemens method (see Patent Literature 1). The Siemens method is a method involving bringing a source gas of silane such as trichlorosilane or mono-silane into contact with a heated silicon core wire and thereby inducing vapor-phase growth (deposition) of polycrystalline silicon on the surface of the silicon core wire by the chemical vapor deposition (CVD) method.

For example, when crystals of monocrystalline silicon are grown by the CZ method, a polycrystalline silicon ingot is charged into a quartz crucible, and a seed crystal is immersed in a silicon melt, into which the polycrystalline silicon ingot is heated and melted, to delete dislocation lines and obtain a dislocation-free crystal, and thereafter the crystal is gradually increased in diameter until a predetermined diameter is reached and then pulled up. During this process, if unmelted polycrystalline silicon remains in the silicon melt, this unmelted polycrystalline piece floats around the solid-liquid interface due to convection and causes loss of crystal lines by inducing generation of dislocation.

Patent Literature 2 reports that needle crystals may be deposited during a process of producing a polycrystalline silicon rod by the Siemens method, and that if single-crystal silicon is grown by the FZ method using such a polycrystalline silicon rod, due to the above-mentioned inhomogeneous microstructure, individual crystallites are not melted homogeneously according to their sizes, but the unmeltable crystallites pass through the melting zone as solid particles toward the single-crystal rod and become incorporated into the solidification surface of the monocrystal as unmelted particles, thereby causing defect formation.

To address this problem, Patent Literature 2 proposes a technique, in which the surface of a sample, which is cut out perpendicularly to the longitudinal direction of the polycrystalline silicon rod, is ground or polished, and after etching, the contrast of the microcrystals of the structure is enhanced to such a degree that the microcrystals are visible even under an optical microscope, and the size and area ratio of needle crystals are measured, and on the basis of the measurement result, whether or not the polycrystalline silicon rod is acceptable as a raw material for growing single-crystal silicon by the FZ method is determined.

CITATION LIST

Patent Literature

Patent Literature 1: Japanese Patent Publication No. 37-18861
Patent Literature 2: Japanese Patent Laid-Open No. 2008-285403

SUMMARY OF INVENTION

Technical Problem

However, visual determination of acceptability under an optical microscope like the technique disclosed in Patent Literature 2 not only is prone to variation of results depending on the degree of etching on the surface of the sample to be observed, the observational skills of the person in charge of evaluation, etc., but also lacks quantitativity and reproducibility. For this reason, it is necessary, from the viewpoint of increasing the production yield of single-crystal silicon, to set the criteria for determining acceptability higher, which results in a higher rate of defective products.

According to studies conducted by the present inventors, it has been also found that the technique disclosed in Patent Literature 2, even when a polycrystalline silicon rod which is determined to be acceptable is used, can cause dislocation and loss of crystal lines during a process of growing a single-crystal silicon rod by the FZ method.

Stable production of single-crystal silicon at a high yield therefore requires a technology for selecting polycrystalline silicon, which is suitable as a raw material for producing single-crystal silicon, with high quantitativity and reproducibility.

Having been made in view of such problems, the present invention aims to provide a technology for selecting polycrystalline silicon, which is suitable as a raw material for producing single-crystal silicon, with high quantitativity and reproducibility, and thereby contributing to stable production of single-crystal silicon.

Solution to Problem

In order to solve the above-described problems, an evaluation method of a degree of crystal orientation of polycrystalline silicon according to the present invention is a method, wherein: a plate-like sample is obtained from the polycrystalline silicon; the plate-like sample is disposed at a position at which a Bragg reflection from a Miller index plane <hkl> is detected; the plate-like sample is rotated in a plane to a rotation angle φ, with the center of the plate-like sample as the rotation center, such that an X-ray irradiation region defined by a slit φ-scans the principal surface of the plate-like sample; a chart is created which indicates dependency of intensity of the Bragg reflection from the Miller index plane <hkl> on the rotation angle (φ) of the plate-like sample; and the degree of crystal orientation of the polycrystalline silicon is evaluated in terms of the number of peaks appearing in the chart.

It is preferable that the Miller index plane <hkl> is <111> or <220>.

It is preferable that peaks of which the S/N ratio is three or larger are counted as the number of peaks appearing in the chart.

A selection method of a polycrystalline silicon rod according to the present invention is a method for selecting a polycrystalline silicon rod which is used as a raw material for producing single-crystal silicon, wherein: the polycrystalline silicon rod is a rod grown through deposition by a chemical vapor deposition method; a plate-like sample of which the principal surface is the cross-section of the polycrystalline silicon rod perpendicular to the radial direction is obtained; the plate-like sample is disposed at a position at which a Bragg reflection from a Miller index plane <hkl> is detected; the plate-like sample is rotated in a plane to a rotation angle φ, with the center of the plate-like sample as the rotation center, such that an X-ray irradiation region defined by a slit φ-scans the principal surface of the plate-like sample; a chart is created which indicates dependency of intensity of the Bragg reflection from the Miller index plane <hkl> on the rotation angle (φ) of the plate-like sample; and the polycrystalline silicon rod is selected as a raw material for producing single-crystal silicon depending on the number of peaks appearing in the chart.

It is preferable that the Miller index plane <hkl> is <111> or <220>.

It is preferable that peaks of which the S/N ratio is three or larger are counted as the number of peaks appearing in the chart.

It is also preferable that a region of the principal surface of the plate-like sample is φ-scanned by the in-plane rotation, and that the polycrystalline silicon rod is selected as a raw material for producing single-crystal silicon if the number of peaks appearing in the chart obtained by the φ-scanning is equal to or smaller than $24/cm^2$ per unit area of the plate-like sample.

It is further preferable that a region of the principal surface of the plate-like sample is φ-scanned by the in-plane rotation, and that a value obtained by multiplying a half-value width (degree) of the peak by $\delta L = 2^{1/2} \pi R_0/360$ (mm/degree), where $R_0$ (mm) is the radius of the plate-like sample, is defined as an inhomogeneous crystal grain size (mm), and a polycrystalline silicon rod of which all the inhomogeneous crystal grain sizes are smaller than 0.5 mm is selected as a raw material for producing single-crystal silicon.

Advantageous Effects of Invention

It is possible to suppress local generation of partial melting residue and contribute to stable production of single-crystal silicon by evaluating a degree of crystal orientation of polycrystalline silicon by the method according to the present invention, and growing crystals by the FZ method using a polycrystalline silicon rod selected as an acceptable one by this evaluation method or growing crystals by the CZ method using an ingot obtained from a polycrystalline silicon block.

DESCRIPTION OF EMBODIMENTS

In the following, embodiments of the present invention will be described with reference to the drawings.

While conducting studies aimed at improving the quality of polycrystalline silicon for stable production of single-crystal silicon, the present inventors have found that, depending on the conditions at the time of deposition of polycrystalline silicon, differences occur in the degree of crystal orientation inside a polycrystalline silicon rod. A block of polycrystalline silicon, unlike that of single-crystal silicon, contains many crystal grains, and it is generally believed that each of these many crystal grains is randomly oriented. According to the studies of the present inventors, however, the crystal grains contained in a polycrystalline silicon block are not always completely random-oriented.

A powder sample which can be obtained by pulverizing a polycrystalline silicon block can be handled on the supposition that the individual silicon crystal grains are completely random-oriented. In fact, the Bragg reflection intensity is substantially constant when the powder sample is disposed at a position at which a Bragg reflection from a specific Miller index plane <hkl> is detected and the powder sample is rotated in a plane, with the center of the sample as the rotation center, such that an X-ray irradiation region defined by a slit scans the entire surface of the powder sample. In other words, the intensity of the Bragg reflection from the above-mentioned Miller index plane <hkl> exhibits no dependency on the rotation angle.

By contrast, when the present inventors extracted plate-like samples, of which the principal surface is the cross-section of a polycrystalline silicon rod perpendicular to the radial direction, from many different polycrystalline silicon rods grown through deposition by the chemical vapor deposition method, and using the same technique as described above, checked for the dependency of the intensity of the Bragg reflection from the Miller index plane <hkl> on the rotation angle, the facts were confirmed that, depending on the production conditions of a polycrystalline silicon rod, the intensity of the Bragg reflection from the Miller index plane <hkl> is dependent on the rotation angle and peaks can appear in a diffraction chart, and the shape and the number of the peaks are also dependent on the production conditions.

That is, crystal grains in a polycrystalline silicon rod are not always random-oriented, but the degree of crystal orientation (random orientation) depends on the conditions at the time of deposition of polycrystalline silicon. It has been proven that, when a polycrystalline silicon rod or a polycrystalline silicon ingot having a relatively high degree of crystal orientation (relatively low random orientation) is used as a raw material for producing single-crystal silicon, partial melting residue can locally occur, which can induce generation of dislocation and even cause loss of crystal lines.

Figure 1A:
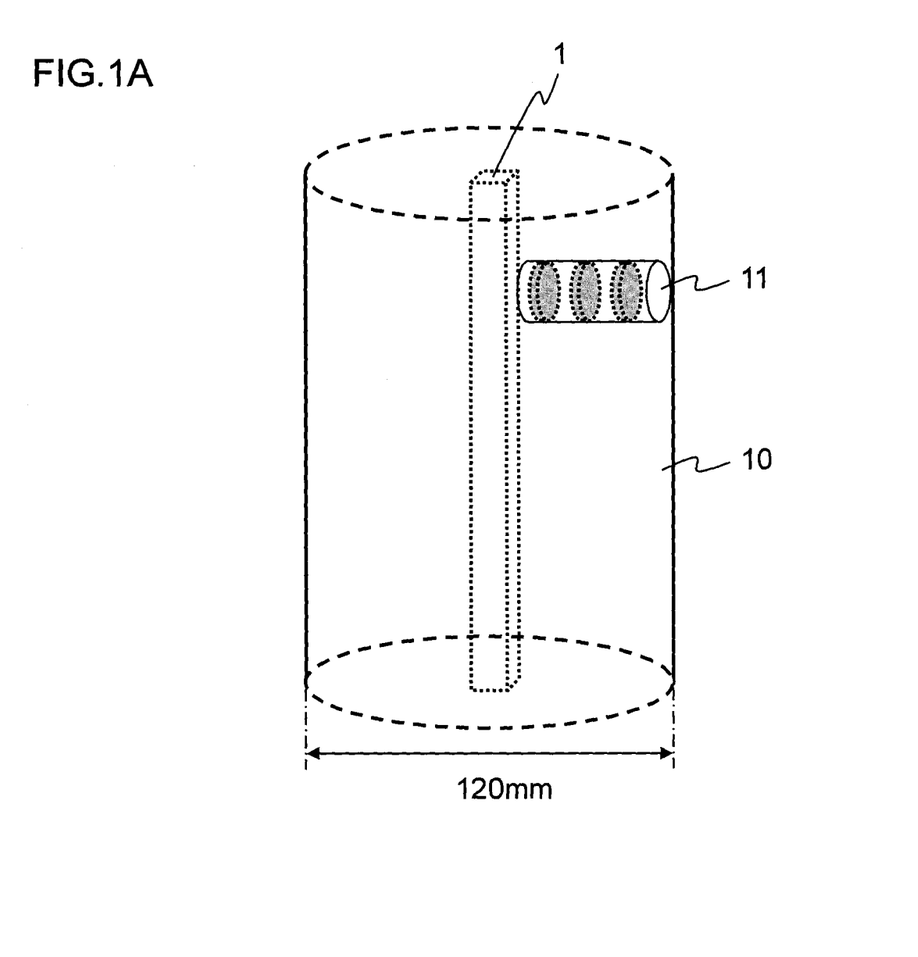
FIG. 1A is a view for illustrating an example of extraction of a plate-like sample used for X-ray diffraction measurement from a polycrystalline silicon rod which is grown through deposition by the chemical vapor deposition method.
Figure 1B:
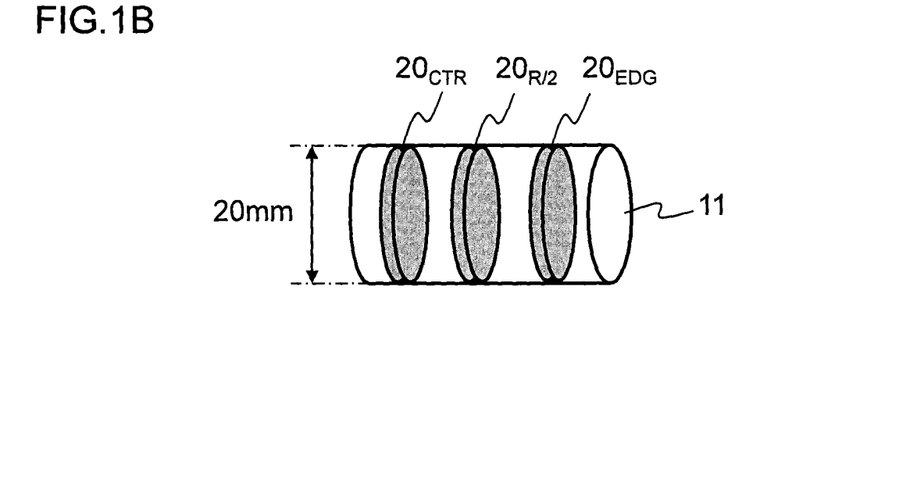
FIG. 1B is a view for illustrating an example of extraction of the plate-like sample used for the X-ray diffraction measurement from the polycrystalline silicon rod which is grown through deposition by the chemical vapor deposition method.

FIG. 1A and FIG. 1B are views for illustrating an example of extraction of a plate-like sample 20 used for X-ray diffraction profile measurement from a polycrystalline silicon rod 10 which is grown through deposition by the chemical vapor deposition method such as the Siemens method. In the figure, the reference sign 1 denotes a silicon core wire, on the surface of which polycrystalline silicon is deposited to make a silicon rod. In this example, the plate-like sample 20 is extracted from three portions (CTR: a portion close to the silicon core wire 1, EDG: a portion close to the side surface of the polycrystalline silicon rod 10, and R/2: a portion between CTR and EDG) in order to check for radial dependency of the degree of crystal orientation of the polycrystalline silicon rod; however, the sample extraction is not limited to extraction from these portions.

The diameter of the polycrystalline silicon rod 10 exemplified in FIG. 1A is roughly 120 mm, and a rod 11 having a diameter of roughly 20 mm and a length of roughly 60 mm is extracted from the side surface side of the polycrystalline silicon rod 10 perpendicularly to the longitudinal direction of the silicon core wire 1.

Then, as shown in FIG. 1B, plate-like samples ($20_{CTR}$, $20_{EDG}$, and $20_{R/2}$), of which the principal surface is the cross-section of the polycrystalline silicon rod 10 perpendicular to the radial direction and the thickness is roughly 2 mm, are extracted from the portion (CTR) close to the silicon core wire 1 of this rod 11, the portion (EDG) close to the side surface of the polycrystalline silicon rod 10, and the portion (R/2) between the portions CTR and EGD, respectively.

The portions of extraction, the length, and the number of the rod 11 may be appropriately determined according to the diameter of the silicon rod 10 or the diameter of the rod 11 to be extracted, and the plate-like sample 20 may also be extracted from any portion of the extracted rod 11; however, it is preferable that the position allows the property of the entire silicon rod 10 to be reasonably estimated.

The diameter of the plate-like sample 20 being roughly 20 mm is also merely an example, and the diameter can be suitably determined within such a range that does not hinder X-ray diffraction measurement.

In the selection method of a polycrystalline silicon rod according to the present invention, the plate-like sample 20 extracted as described above is disposed at positions at which a Bragg reflection from a Miller index plane <hkl> is detected, the plate-like sample 20 is rotated in a plane to a rotation angle $\phi$, with the center of the plate-like sample 20 as the rotation center, such that an X-ray irradiation region defined by a slit $\phi$-scans the principal surface of the plate-like sample 20, a chart is created which indicates the dependency of the intensity of the Bragg reflection from the Miller index plane <hkl> on the rotation angle ($\phi$) of the plate-like sample 20, and the polycrystalline silicon is selected as a raw material for producing single-crystal silicon depending on the number of peaks appearing in the chart.

Figure 2:
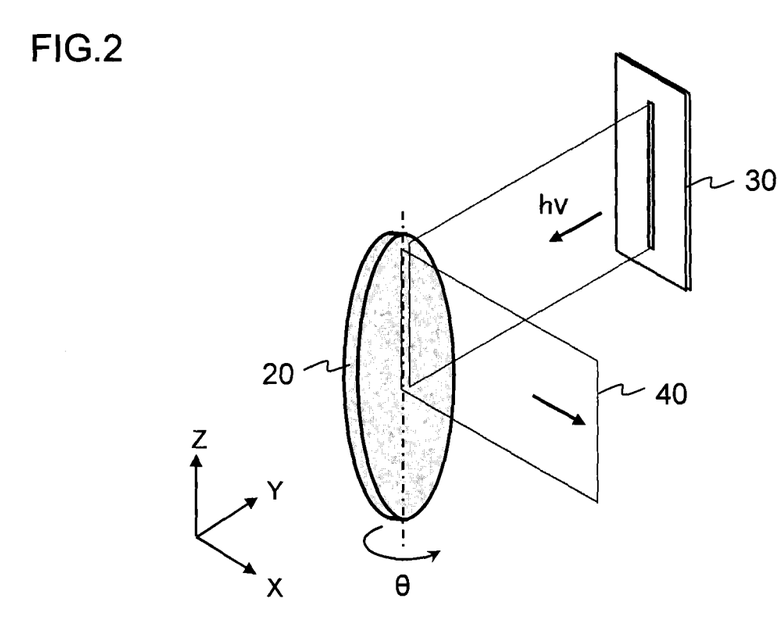
FIG. 2 is a view for illustrating the outline of an example measurement system for obtaining an X-ray diffraction profile from a plate-like sample by the so-called θ-2θ method.

FIG. 2 is a view for illustrating the outline of an example measurement system for obtaining an X-ray diffraction profile from the plate-like sample 20 by the so-called $\theta$-2$\theta$ method. An X-ray beam 40 (Cu—K$\alpha$ ray: wavelength 1.54 Å) emitted from a slit 30 and collimated enters the plate-like sample 20, and while the plate-like sample 20 is being rotated in the XY-plane, the intensity of the diffracted X-ray beam at each rotation angle ($\theta$) of the sample is detected with a detector (not shown) to obtain a $\theta$-2$\theta$ X-ray diffraction chart.

Figure 3:
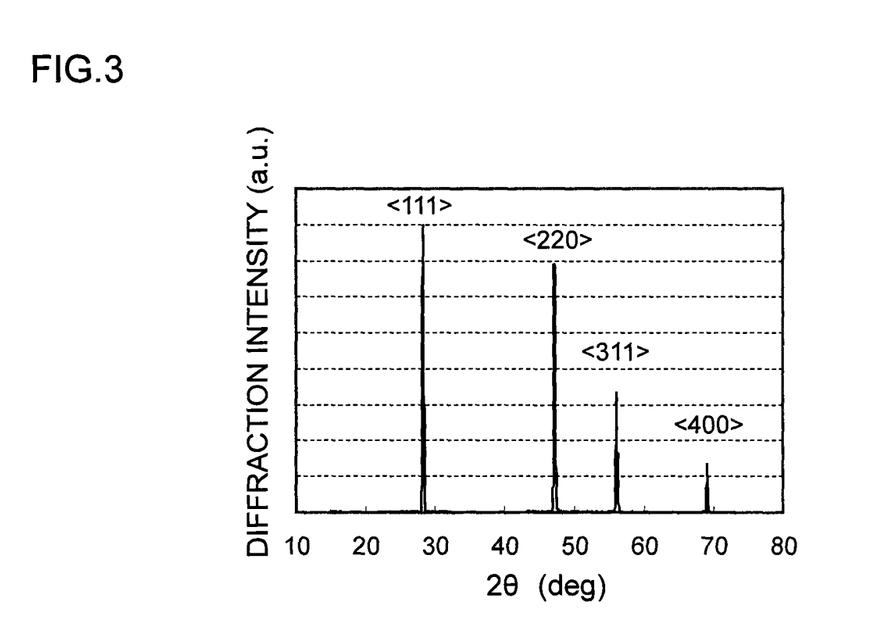
FIG. 3 is one example of a chart of the θ-2θ X-ray diffraction.

FIG. 3 is an example of the $\theta$-2$\theta$ X-ray diffraction chart obtained by the above method, and in this chart, intense Bragg reflections from the Miller index planes <111>, <220>, <311>, and <400> appear as peaks at the positions of 2$\theta$=28.40°, 47.24°, 55.98°, and 68.98°, respectively.

Figure 4:
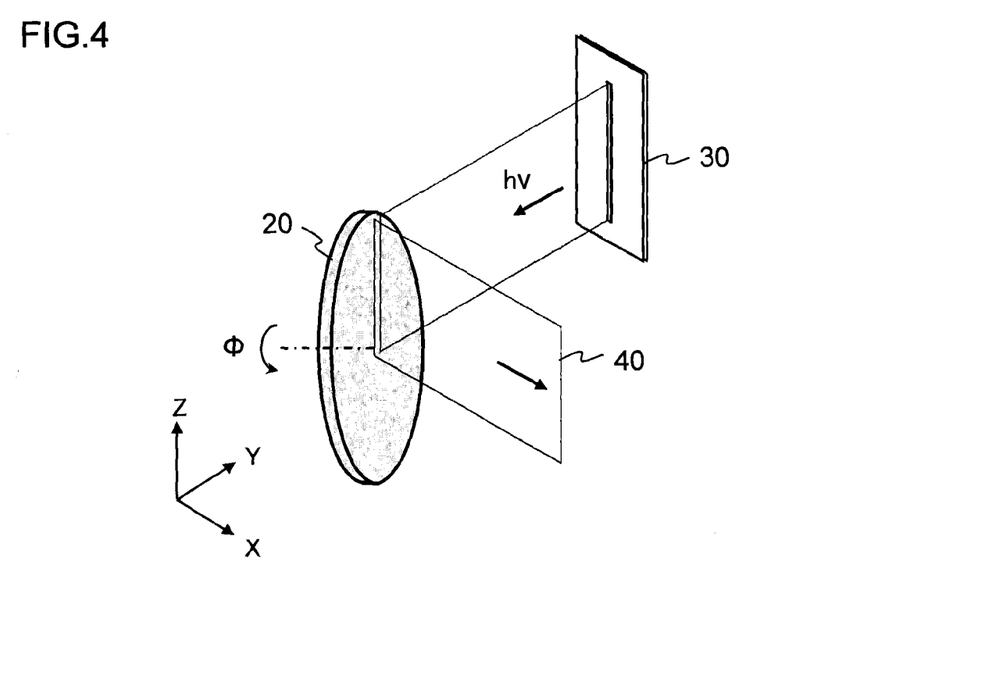
FIG. 4 is a view for illustrating the outline of an example measurement system for obtaining an X-ray diffraction profile from a plate-like sample by the so-called φ-scanning method.

FIG. 4 is a view for illustrating the outline of a measurement system for obtaining an X-ray diffraction profile from the plate-like sample 20 by the so-called $\phi$-scanning method. For example, when the above-described $\theta$ of the plate-like sample 20 is assumed to be the angle at which a Bragg reflection from the Miller index plane <111> is detected, and in this state, a thin rectangular region defined by a slit in a region from the center to the circumferential edge of the plate-like sample 20 is irradiated with an X-ray, and the plate-like sample 20 is rotated ($\phi$=0° to 360°) in the YZ-plane, with the center of the plate-like sample 20 as the rotation center, such that the X-ray irradiation region scans the entire surface of the plate-like sample 20.

Figure 5:
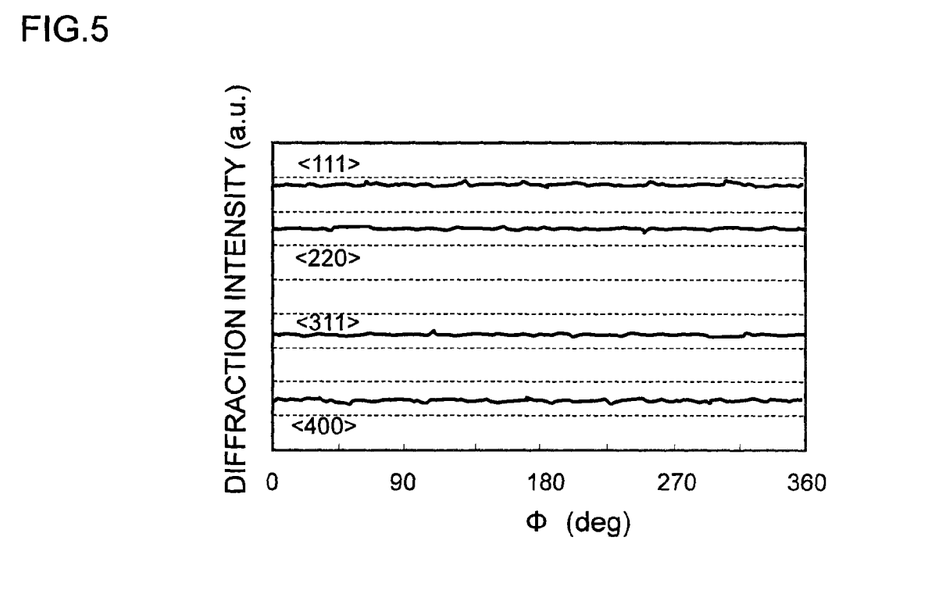
FIG. 5 is one example of a chart obtained by performing the φ-scanning measurement shown in FIG. 4 on Miller index planes <111>, <220>, <311>, and <400>.

FIG. 5 is one example of the chart obtained by performing the above-described $\phi$-scanning measurement on the Miller index planes <111>, <220>, <311>, and <400>. In this example, the Bragg reflection intensity is substantially constant in any of the above-mentioned Miller index planes, and without the dependency of the Bragg reflection intensity on the rotation angle $\phi$, the chart is similar to that of a powder sample. That is, this plate-like sample 20 can be determined to have a low degree of crystal orientation (high random orientation).

Figure 6:
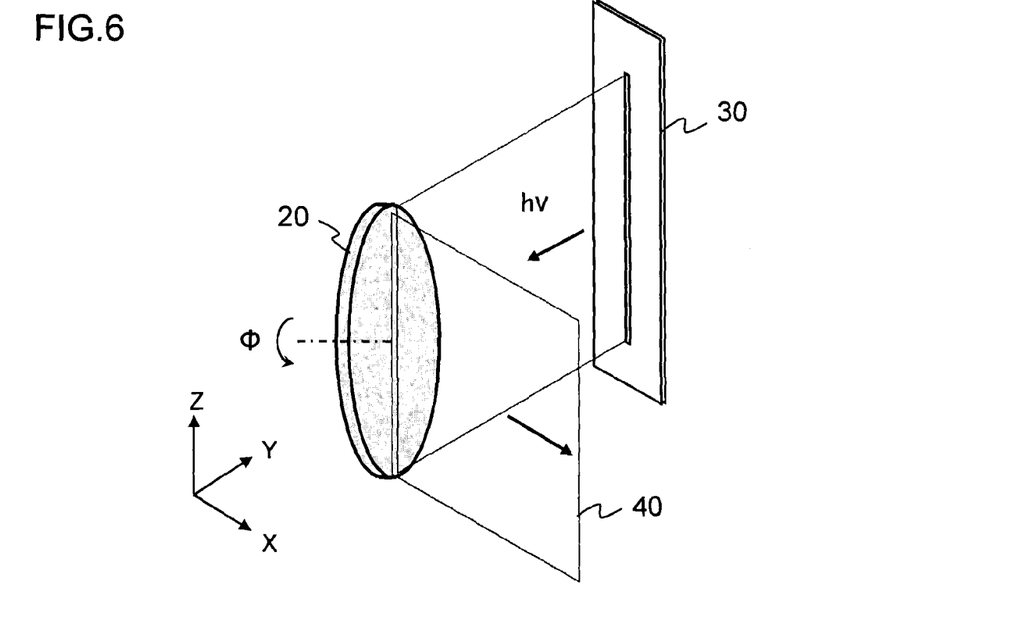
FIG. 6 is a view for illustrating the outline of another example measurement system for obtaining an X-ray diffraction profile from a plate-like sample by the φ-scanning method.

FIG. 6 is a view for illustrating the outline of another example measurement system for obtaining an X-ray diffraction profile from the plate-like sample 20 by the $\phi$-scanning method, and in the example shown in this figure, a thin rectangular region defined by the slit in a region across both the circumferential edges of the plate-like sample 20 is irradiated with an X-ray, and the plate-like sample 20 is rotated ($\phi$=0° to 180°) in the YZ-plane, with the center of the plate-like sample 20 as the rotation center, such that the X-ray irradiation region scans the entire surface of the plate-like sample 20.

Figure 7:
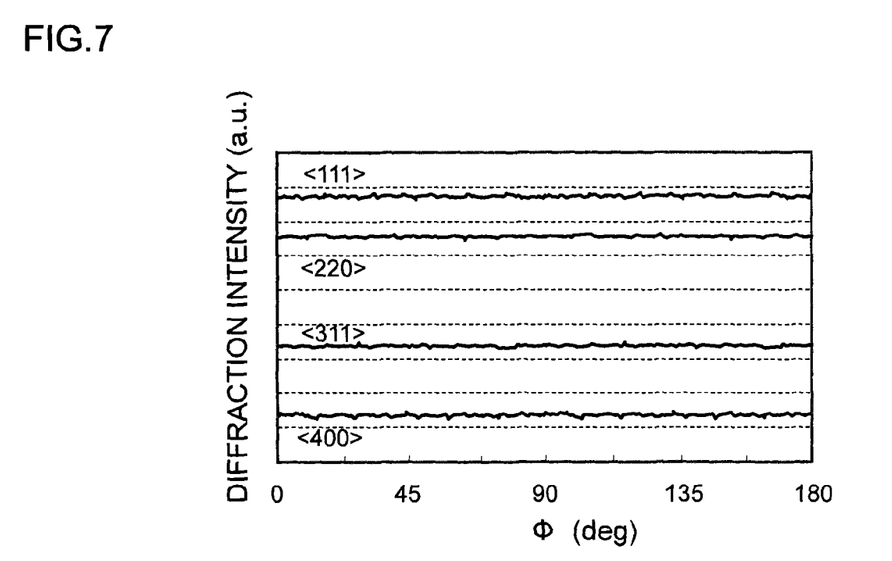
FIG. 7 is one example of a chart obtained by performing the φ-scanning measurement shown in FIG. 6 on Miller index planes <111>, <220>, <311>, and <400>.

FIG. 7 is one example of the chart obtained by performing the above-described $\phi$-scanning measurement on the Miller index planes <111>, <220>, <311>, and <400>, and a $\phi$-scanning chart which is substantially the same as that shown in FIG. 5 is obtained.

Figure 8:
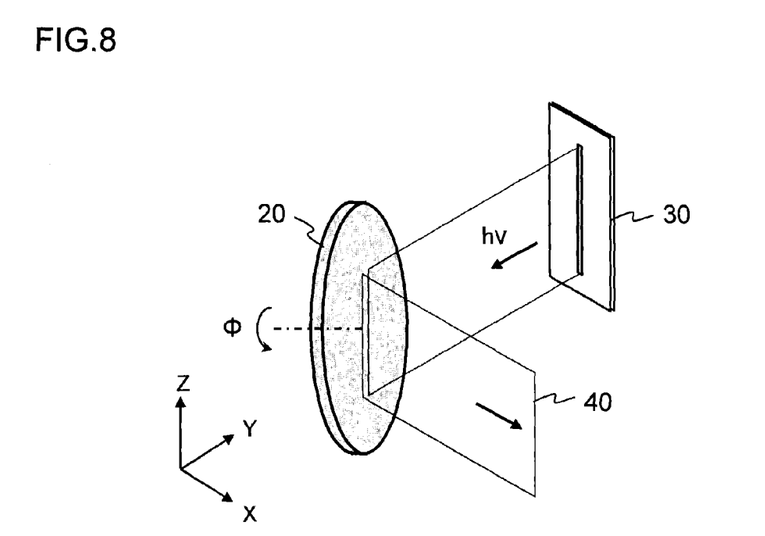
FIG. 8 is a view for illustrating the outline of another example measurement system for obtaining an X-ray diffraction profile from a plate-like sample by the φ-scanning method.

FIG. 8 is a view for illustrating the outline of yet another example measurement system for obtaining an X-ray diffraction profile from the plate-like sample 20 by the $\phi$-scanning method, and in the example shown in this figure, only the inner circumferential region of the plate-like sample 20 instead of its entire principal surface is irradiated with an X-ray, and the plate-like sample 20 is rotated ($\phi$=0° to 180°) in the YZ-plane, with the center of the plate-like sample 20 as the rotation center, such that the X-ray irradiation region scans the entire surface of the plate-like sample 20.

It is also possible to obtain the distribution of degree of crystal orientation in the plane of the plate-like sample 20 by performing a processing such as identifying the difference between the $\phi$-scanning chart obtained from such an inner circumferential X-ray irradiation region and the above-described $\phi$-scanning chart obtained from the entire principal surface of the plate-like sample 20.

While it is unlikely that distribution of degree of crystal orientation occurs in the plane of the plate-like sample 20 which is extracted in the aspect as shown in FIGS. 1A and 1B, needless to say, the evaluation of crystal orientation according to the present invention is significant not only as a selection method of a polycrystalline silicon rod grown by the Siemens method, etc., but also as a method for evaluating a degree of crystal orientation of polycrystalline silicon by the X-ray diffraction method. For example, it is also possible to know presence or absence of crystal orientation inside a polycrystalline silicon rod, or a change in crystal orientation with the increasing diameter of a polycrystalline silicon rod, etc. by identifying the distribution of degree of crystal orientation in the plane of a plate-like plate which is cut out parallel to the radial direction of a polycrystalline silicon rod grown through deposition by the chemical vapor deposition method.

As described above, when the degree of crystal orientation is low (the random orientation is high), the Bragg reflection intensity does not depend on the rotation angle $\phi$, and no peak is found in the $\phi$-scanning chart; however, when an evaluation similar to the above is made on the plate-like sample 20 which is extracted from a polycrystalline silicon rod obtained under different conditions, peaks can appear in the $\phi$-scanning chart.

Figure 9:
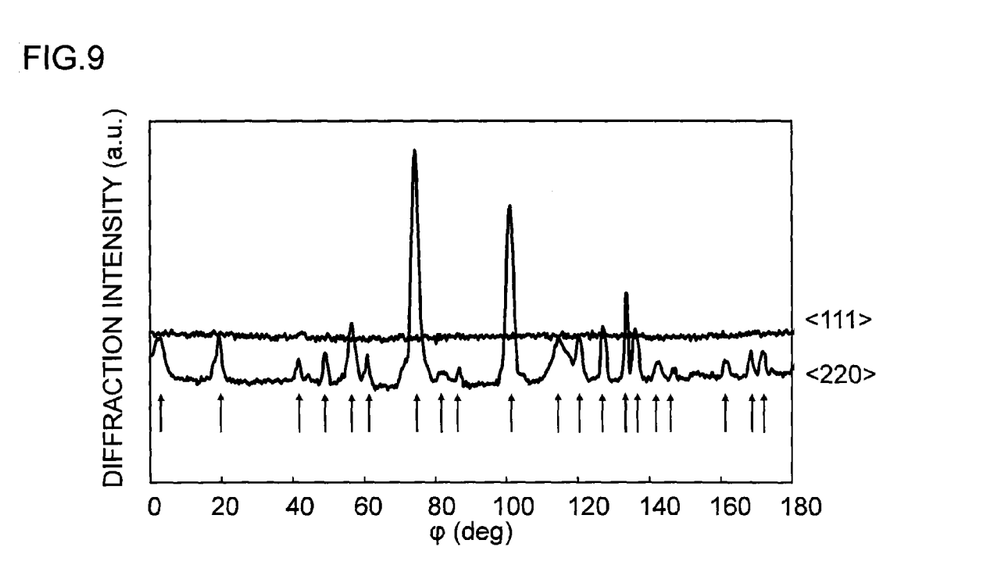
FIG. 9 is one example of a φ-scanning chart obtained for the Miller index planes <111> and <220> in which an intense Bragg reflection is obtained from a silicon crystal.

FIG. 9 is one such example, and shows a $\phi$-scanning chart obtained by the measurement of the aspect shown in FIG. 8 for the Miller index planes <111> and <220> in which an intense Bragg reflection is obtained from the silicon crystal. The peaks indicated by the arrows in the figure are peaks of which the S/N ratio is three or larger, and over the entire measurement rotation angle $\phi$ of 0° to 180°, zero peak and 20 peaks were counted for the Miller index planes <111> and <220>, respectively.

While the details of results of experiments conducted by the present inventors will be described later, according to studies of the present inventors, the smaller the number of peaks counted by the above-described method, and the narrower the half-value width of the peak, the more suitable as a raw material for producing single-crystal silicon. This is probably because such polycrystalline silicon has a low degree of crystal orientation (high random orientation), and when such a polycrystalline silicon rod or a polycrystalline silicon ingot is used as a raw material for producing single-crystal silicon, partial melting residue is less likely to locally occur, and as a result, loss of crystal lines attributable to generation of dislocation induced is less likely to occur.

More specifically, it is preferable that the number of peaks appearing in the $\phi$-scanning chart is, for both the Miller index planes <111> and <220>, equal to or smaller than 24/cm$^2$ when converted into unit per area of the plate-like sample.

It is also preferable that the value obtained by multiplying the half-value width (degree) of the above-described peak by $\delta L=2^{1/2}\pi R_0/360$ (mm/degree), where $R_0$ (mm) is the radius of the plate-like sample, is defined as an inhomogeneous crystal grain size (mm), and that a polycrystalline silicon rod of which all the inhomogeneous crystal grain sizes are smaller than 0.5 mm is selected as a raw material for producing single-crystal silicon. The term inhomogeneous crystal grain size is used for expressing an imaginary size of the crystal grain which gives the above-described peak in a $\phi$-scanning chart, which is not supposed to occur in a polycrystalline silicon with a low degree of crystal orientation, and the term represents, so to speak, an imaginary grain size of a crystal grain existing in a locally oriented state.

Here, the calculation of the inhomogeneous crystal grain size will be described.

Figure 10:
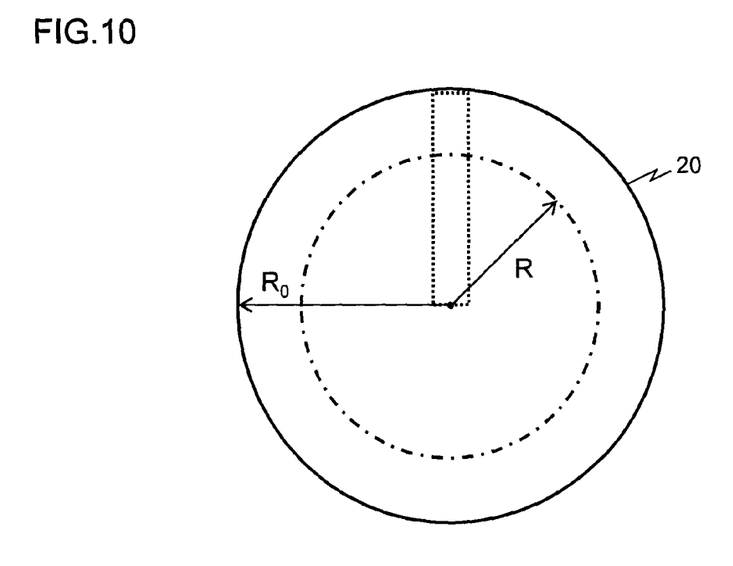
FIG. 10 is a view for illustrating the definition of δL for calculating an inhomogeneous crystal grain size.

FIG. 10 is a view for illustrating the definition of $\delta L$ ($=2^{1/2}\pi R_0/360$) for calculating the inhomogeneous crystal grain size, and the region indicated by the dashed line in the figure is the X-ray irradiation region defined by the slit. For example, as shown in FIG. 4 and FIG. 6, when the entire region of the principal surface of the plate-like sample 20 is $\phi$-scanned by in-plane rotation, since the radius of the plate-like sample 20 is $R_0$ (mm), the area $S_0$ of the plate-like sample is $S_0=\pi R_0^2$, and the radius R of the inner region having an area $S$ ($=S_0/2$), which is half the area $S_0$, is $R=R_0/2^{1/2}$.

Since the X-ray irradiation region defined by the slit is rectangular, the region outside the radius R is scanned earlier than the region inside the radius R, and the scanning speed on the circumference of the radius R may be considered to be a medium speed between the scanning speeds in the two regions. Therefore, in the present invention, this scanning speed on the circumference of the radius R is handled as a reference, and the above-described inhomogeneous crystal grain size is calculated on the basis of this speed.

The circumference of the radius R is $2\pi R$, and the value $\delta L$ obtained by dividing $2\pi R$ by 360° (line segment per 1°) is $\delta L = 2\pi R/360° = 2^{1/2}\pi R_0/360°$.

Figure 11:
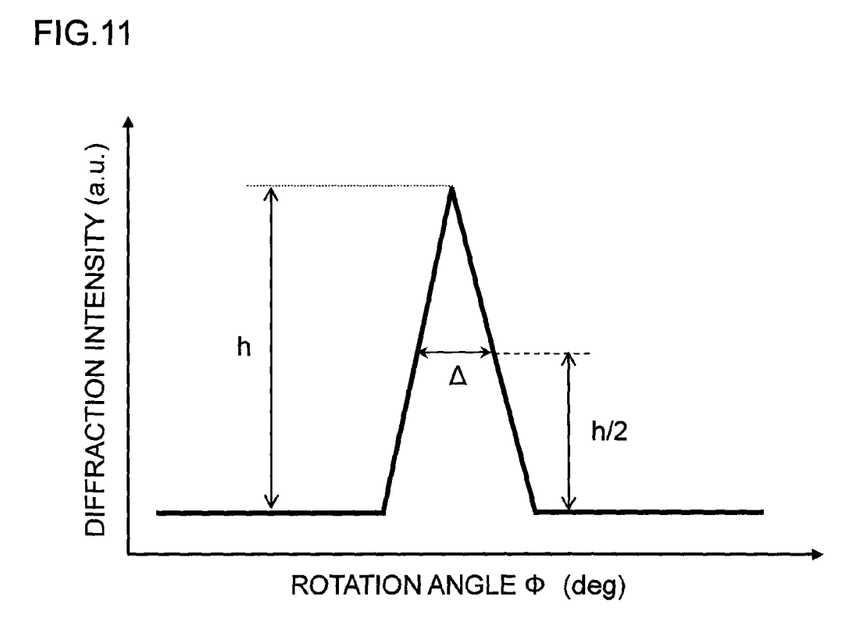
FIG. 11 is a view for illustrating a half-value width of a peak.

When there is a peak as shown in FIG. 11, assuming that the range of the rotation angle $\phi$ which gives ½ of the maximum intensity h is a half-value width $\Delta$, the value obtained by multiplying this peak half-value width $\Delta$ by the above-mentioned $\delta L$ ($=2^{1/2}\pi R_0/360$) is defined as the inhomogeneous crystal grain size.

According to the method of the present invention, the number of peaks allows evaluation of the density of an orientation region where melting residue is likely to locally occur, and the above-described inhomogeneous crystal grain size allows evaluation of the size of such a region. It is then possible to contribute to stable production of single-crystal silicon by eliminating in advance a polycrystalline silicon rod or a polycrystalline silicon ingot containing such orientation regions from the raw material for producing single-crystal silicon.

While in the above description the case was assumed where the entire region of the principal surface of the plate-like sample 20 is $\phi$-scanned by in-plane rotation, the inhomogeneous crystal grain size can be defined also when, for example, as shown in FIG. 8, only the inner circumferential region of the plate-like sample 20, instead of the entire principal surface, is irradiated with an X-ray, and the plate-like sample 20 is rotated ($\phi$=0° to 180°) in the YZ-plane, with the center of the plate-like sample 20 as the rotation center, such that the X-ray irradiation region scans the entire surface of the plate-like sample 20. In this case, the radius of the circular X-ray irradiation region, which is the $\phi$-scanning region, can be adopted as the value of the above-described $R_0$ (mm).

Incidentally, according to studies of the present inventors, even with a polycrystalline silicon in which no crystal grain is recognized by visual observation as disclosed in Patent Literature 2, loss of crystal lines can occur due to generation of dislocation inducted, when single-crystal silicon is produced using such silicon as a raw material. As will be described later, according to the method of the present invention, the degree of such loss of crystal lines is significantly lowered, which has confirmed that the method of the present invention has a high quantitativity and reproducibility.

In particular, when single-crystal silicon was produced using as a raw material a polycrystalline silicon rod, of which the number of peaks appearing in the $\phi$-scanning chart was equal to or smaller than 24/cm$^2$ by conversion into unit per area of the plate-like sample for both the Miller index planes <111> and <220>, and all the inhomogeneous crystal grain sizes calculated from the peak half-value width were smaller than 0.5 mm, a single-crystal silicon rod without loss of crystal lines was obtained by one FZ processing. Also when single-crystal silicon was grown by the CZ method using as a raw material a silicon ingot obtained by pulverizing such a polycrystalline silicon rod, no loss of crystal lines was found.

EXAMPLES

Four polycrystalline silicon rods grown under different deposition conditions were prepared. For each of these polycrystalline silicon rods (silicon rods A to D), roughly 2 mm thick plate-like samples ($20_{CTR}$, $20_{EDG}$, and $20_{R/2}$) were extracted from the three portions shown in FIGS. 1A and 1B, and by the measurement system shown in FIG. 6, a φ-scanning chart for the Miller index planes <111> and <220> was obtained. The diameter of the plate-like sample 20 was approximately 20 mm.

Table 1 summarizes, for each plate-like sample obtained from these polycrystalline silicon rods, the number of peaks (converted into unit per area) and the maximum value (maximum grain size) of the inhomogeneous crystal grain size calculated from these peaks, as well as whether there was loss of crystal lines when a single-crystal silicon rod was grown by the FZ method using the polycrystalline silicon rod.

TABLE 1

| Silicon rod | Plate-like sample | Number of peaks ($cm^2$) | | Maximum grain size (mm) | | Loss of crystal line |
|---|---|---|---|---|---|---|
| | | <111> | <220> | <111> | <220> | |
| A | $20_{CTR}$ | 0 | 0 | — | — | Without loss |
| | $20_{R/2}$ | 0 | 0 | — | — | |
| | $20_{EDG}$ | 0 | 0 | — | — | |
| B | $20_{CTR}$ | 0 | 10 | — | 0.25 | Without loss |
| | $20_{R/2}$ | 0 | 16 | — | 0.25 | |
| | $20_{EDG}$ | 0 | 24 | — | 0.25 | |
| C | $20_{CTR}$ | 17 | 1 | 0.20 | 0.25 | With loss |
| | $20_{R/2}$ | 34 | 12 | 0.30 | 0.45 | |
| | $20_{EDG}$ | 29 | 14 | 0.20 | 0.20 | |
| D | $20_{CTR}$ | 19 | 11 | 0.30 | 0.50 | With loss |
| | $20_{R/2}$ | 14 | 10 | 0.50 | 0.45 | |
| | $20_{EDG}$ | 8 | 5 | 0.30 | 0.65 | |

As shown in Table 1, in the silicon rods A and B, no loss of crystal lines was found when a single-crystal silicon rod was grown by the FZ method, whereas loss of crystal lines occurred in the silicon rods C and D.

With the polycrystalline silicon rods which caused no loss of crystal lines, the number of peaks is 24 per unit area even in the plate-like sample ($20_{EDG}$ of the silicon rod B) in which the most peaks were counted. The inhomogeneous crystal grain size equal to or larger than 0.5 mm was not found in any one of the plate-like samples.

By contrast, plate-like samples in which the number of peaks exceeds 24 per unit area were extracted from the polycrystalline silicon rods which caused loss of crystal lines, and the inhomogeneous crystal grain size equal to or larger than 0.5 mm was found from the polycrystalline silicon rod D.

From these results, the number of peaks appearing in the φ-scanning chart being equal to or smaller than $24/cm^2$ per unit area of the plate-like sample, and all the inhomogeneous crystal grain sizes being smaller than 0.5 mm can be adopted as the criteria for selecting a polycrystalline silicon rod as a raw material for producing single-crystal silicon.

INDUSTRIAL APPLICABILITY

The present invention provides a technology for selecting polycrystalline silicon, which is suitable as a raw material for producing single-crystal silicon, with a high quantitativity and reproducibility, and thereby contributing to stable production of single-crystal silicon.

REFERENCE SIGNS LIST

1 Silicon core wire
10 Polycrystalline silicon rod
11 Rod
20 Plate-like sample
30 Slit
40 X-ray beam

The invention claimed is:
1. An evaluation method of a degree of crystal orientation of polycrystalline silicon by an X-ray diffraction method, the method comprising
    positioning a plate-like sample from the polycrystalline silicon, such that a Bragg reflection from a Miller index plane <hkl> is detected,
    rotating the plate-like sample in a plane to a rotation angle φ, with the center of the plate-like sample as the rotation center, such that an X-ray irradiation region defined by a slit φ-scans the principal surface of the plate-like sample,
    creating a chart which indicates dependency of intensity of the Bragg reflection from the Miller index plane <hkl> on the rotation angle (φ) of the plate-like sample, and
    evaluating the degree of crystal orientation of the polycrystalline silicon in terms of the number of peaks appearing in the chart.
2. The method according to claim 1, wherein the Miller index plane <hkl> is <111> or <220>.
3. The method according to claim 1, wherein peaks of which the S/N ratio is three or larger are counted as the number of peaks appearing in the chart.
4. A selection method of a polycrystalline silicon rod, the method comprising
    growing a polycrystalline silicon rod by a chemical vapor deposition method,
    extracting a plate-like sample of which the principal surface is the cross-section of the polycrystalline silicon rod perpendicular to the radial direction,
    positioning the plate-like sample such that a Bragg reflection from a Miller index plane <hkl> is detected,
    rotating the plate-like sample in a plane to a rotation angle φ, with the center of the plate-like sample as the rotation center, such that an X-ray irradiation region defined by a slit φ-scans the principal surface of the plate-like sample,
    creating a chart which indicates dependency of intensity of the Bragg reflection from the Miller index plane <hkl> on the rotation angle (φ) of the plate-like sample, and
    selecting the polycrystalline silicon rod as a raw material for producing single-crystal silicon depending on the number of peaks appearing in the chart,
    wherein a region of the principal surface of the plate-like sample is φ-scanned by the in-plane rotation, and the polycrystalline silicon rod is selected as a raw material for producing single-crystal silicon if the number of peaks appearing in the chart obtained by the φ-scanning is equal to or smaller than $24/cm^2$ per unit area of the plate-like sample.
5. The method according to claim 4, wherein the Miller index plane <hkl> is <111> or <220>.
6. The method according to claim 4, wherein peaks of which the S/N ratio is three or larger are counted as the number of peaks appearing in the chart.
7. A selection method of a polycrystalline silicon rod, the method comprising growing a polycrystalline silicon rod by a chemical vapor deposition method, extracting a plate-like sample of which the principal surface is the cross-section of the polycrystalline silicon rod perpendicular to the radial direction, positioning the plate-like sample such that a Bragg reflection from a Miller index plane <hkl> is detected, rotating the plate-like sample in a plane to a rotation angle $\phi$, with the center of the plate-like sample as the rotation center, such that an X-ray irradiation region defined by a slit $\phi$-scans the principal surface of the plate-like sample, creating a chart which indicates dependency of intensity of the Bragg reflection from the Miller index plane <hkl> on the rotation angle ($\phi$) of the plate-like sample, and selecting the polycrystalline silicon rod as a raw material for producing single-crystal silicon depending on the number of peaks appearing in the chart, wherein a region of the principal surface of the plate-like sample is $\phi$-scanned by the in-plane rotation, and the value obtained by multiplying a half-value width (degree) of the peak by $\delta L = 2^{1/2} \pi R_0 / 360$ (mm/degree), where $R_0$ (mm) is the radius of the plate-like sample, is defined as an inhomogeneous crystal grain size (mm), and a polycrystalline silicon rod of which all the inhomogeneous crystal grain sizes are smaller than 0.5 mm is selected as a raw material for producing single-crystal silicon.

8. The method according to claim 4, wherein the polycrystalline silicon rod is grown by the Siemens method.

9. A polycrystalline silicon rod selected by the method according to claim 4.

10. A polycrystalline silicon ingot obtained by pulverizing the polycrystalline silicon rod according to claim 9.

11. A production method of single-crystal silicon, the method comprising preparing single-crystal silicon using as a raw material the polycrystalline silicon rod according to claim 9.

12. A production method of single-crystal silicon the method comprising preparing single-crystal silicon using the polycrystalline silicon ingot according to claim 10 as a raw material.

13. The method according to claim 7, wherein the Miller index plane <hkl> is <111> or <220>.

14. The method according to claim 7, wherein peaks of which the S/N ratio is three or larger are counted as the number of peaks appearing in the chart.

15. The method according to claim 7, wherein the polycrystalline silicon rod is grown by the Siemens method.

16. A polycrystalline silicon rod selected by the method according to claim 7.

17. A polycrystalline silicon ingot obtained by pulverizing the polycrystalline silicon rod according to claim 16.

18. A production method of single-crystal silicon, the method comprising preparing single-crystal silicon using as a raw material the polycrystalline silicon rod according to claim 16.

19. A production method of single-crystal silicon the method comprising preparing single-crystal silicon using the polycrystalline silicon ingot according to claim 17 as a raw material.

* * * * *